US008513615B2

(12) United States Patent (10) Patent No.: US 8,513,615 B2
Chen et al. (45) Date of Patent: Aug. 20, 2013

(54) MILLIMETER-WAVE INSPECTION APPARATUS

(75) Inventors: Zhiqiang Chen, Beijing (CN); Ziran Zhao, Beijing (CN); Yuanjing Li, Beijing (CN); Wanlong Wu, Beijing (CN); Yinong Liu, Beijing (CN); Li Zhang, Beijing (CN); Dong Lin, Beijing (CN); Zongjun Shen, Beijing (CN); Xilei Luo, Beijing (CN); Zhimin Zheng, Beijing (CN); Yingkang Jin, Beijing (CN); Shuo Cao, Beijing (CN); Bin Sang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 146 days.

(21) Appl. No.: 13/126,067

(22) PCT Filed: Dec. 29, 2010

(86) PCT No.: PCT/CN2010/080429
§ 371 (c)(1),
(2), (4) Date: Apr. 26, 2011

(87) PCT Pub. No.: WO2011/079790
PCT Pub. Date: Jul. 7, 2011

(65) Prior Publication Data
US 2012/0085909 A1  Apr. 12, 2012

(30) Foreign Application Priority Data

Jun. 30, 2010 (CN) .......................... 2010 1 0223333

(51) Int. Cl.
*G01J 5/02* (2006.01)
(52) U.S. Cl.
USPC ...................................... 250/382; 250/338.1

(58) Field of Classification Search
USPC .......................................................... 250/382
See application file for complete search history.

(56) References Cited

U.S. PATENT DOCUMENTS

| 4,015,896 A * | 4/1977 | Sonnet ........................... 359/736 |
| 5,047,783 A | 9/1991 | Hugenin ........................ 342/179 |

(Continued)

FOREIGN PATENT DOCUMENTS

| CN | 1170306 | 1/1998 |
| CN | 101644770 | 2/2010 |

(Continued)

OTHER PUBLICATIONS

First Chinese Office for Chinese Application No. 201010223333.2, dated Nov. 5, 2012, 5 pages.
Written Opinion of the International Search Report in Chinese for PCT/CN2010/080429 filed Dec. 28, 2010; 10 pages.
Supplemental European Search Report for European Application No. 10838372.0-1240 (PCT/CN2010/080429), search completed Jun. 13, 2012, 11 pages.
European Office Action from EP 10838372.0, dated May 16, 2013.

*Primary Examiner* — David Porta
*Assistant Examiner* — Djura Malevic
(74) *Attorney, Agent, or Firm* — Westman, Champlin & Kelly, P.A.

(57) ABSTRACT

The present invention discloses a millimeter-wave inspection apparatus. The millimeter-wave inspection apparatus comprises: optics devices, configured to receive millimeter-wave energy radiated from an object to be inspected and focus the received millimeter-wave energy; a radiometer receiving device configured to receive the focused millimeter-wave energy and transform the millimeter-wave energy into electrical signal; and an imaging device configured to generate a temperature image of the object to be inspected based on the electrical signal. Compared with the prior art, the millimeter-wave inspection apparatus of the present invention has a simple and compact structure; it would not be harmful to the human health by employing the passive millimeter-wave human body security inspection technology. With the above configuration, the contraband items to be concealed within the human clothing can be efficiently and effectively detected.

19 Claims, 9 Drawing Sheets

(56) References Cited

U.S. PATENT DOCUMENTS

| | | | |
|---|---|---|---|
| 5,760,397 A * | 6/1998 | Huguenin et al. | 250/332 |
| 6,353,224 B1 * | 3/2002 | Sinclair et al. | 250/336.1 |
| 7,583,074 B1 * | 9/2009 | Lynch et al. | 324/120 |
| 8,213,672 B2 * | 7/2012 | Daly et al. | 382/100 |
| 2002/0044276 A1 * | 4/2002 | Stoner et al. | 356/141.1 |
| 2008/0290265 A1 * | 11/2008 | Daly et al. | 250/252.1 |
| 2009/0041292 A1 * | 2/2009 | Daly et al. | 382/100 |
| 2010/0069782 A1 * | 3/2010 | Icove et al. | 600/549 |
| 2010/0193688 A1 * | 8/2010 | Koch et al. | 250/338.1 |
| 2010/0264316 A1 * | 10/2010 | Delaney et al. | 250/358.1 |
| 2011/0133087 A1 * | 6/2011 | Mann et al. | 250/338.4 |

FOREIGN PATENT DOCUMENTS

| | | |
|---|---|---|
| WO | 9007130 | 6/1990 |
| WO | WO03/029772 | 4/2003 |
| WO | 2006129113 A1 | 12/2006 |
| WO | 2009157552 A1 | 12/2009 |

\* cited by examiner

MILLIMETER-WAVE INSPECTION APPARATUS

CROSS-REFERENCE TO RELATED APPLICATION

This Application is a Section 371 National Stage Application of International Application No. PCT/CN2010/080429, filed Dec. 29, 2010 and not yet published, which claims the benefit of Chinese Patent Application No. 201010223333.2 filed on Jun. 30, 2010 in the State Intellectual Property Office of China, the contents of which are hereby incorporated by reference in their entirety.

FIELD OF INVENTION

The present invention relates to a human body security inspection apparatus, more particularly, to a millimeter-wave inspection apparatus for human body inspection.

BACKGROUND OF INVENTION

It is known in the art that human body security inspection apparatus mainly includes metal detectors, trace inspection equipment as well as x-ray transmission apparatus. Specifically, the metal detectors are only sensitive to the metallic substance; trance inspection equipment is merely effective to inspect explosive and drugs, whereas x-ray transmission apparatus can only detect metallic/non-metallic articles, explosive, and drugs and so on. Furthermore, the x-ray transmission apparatus can have a relatively high space resolution and a certain scanning speed, but is harmful to the human body to a certain degree, due to ionizing radiation of the x-ray. Therefore, they are limited to be employed in the human body security inspection.

In order to satisfy the demand for the human body security inspection without harming the human body, it is essential to provide a millimeter-wave inspection apparatus, which at least alleviates or fully eliminates at least one of the above mentioned technical problems.

SUMMARY OF INVENTION

Bearing in mind of the above shortages in prior arts, an object of the present invention is to alleviate at least one aspect of the above problems and defects.

Accordingly, one object of the present invention is to provide a millimeter-wave inspection apparatus to perform security inspection of the human body.

According one aspect of the present invention, there is provided a millimeter-wave inspection apparatus. The millimeter-wave inspection apparatus includes: optics devices, configured to receive millimeter-wave energy radiated from an object to be inspected and focus the received millimeter-wave energy; a radiometer receiving device configured to receive the focused millimeter-wave energy and transform the millimeter-wave energy into electrical signal; and an imaging device configured to generate a temperature image of the object to be inspected in accordance with the electrical signal.

In one embodiment, the optics device further includes: a swing reflection device configured to receive and reflect the millimeter-wave energy from the object to be inspected; a convex lens device configured to focus the millimeter-wave energy from the swing reflection device; and a path-folding reflection plate device configured to fold the propagating path of the focused millimeter-wave energy.

In one embodiment, the swing reflection device comprises: a support frame, a swing reflection plate which is rotatably supported onto the support frame; and a first driving motor, which is connected to the swing reflection plate, so as to sway the swing reflection plate back and forth.

Preferably, the support frame comprises: a first support plate, a second support plate which is disposed to be in parallel with and opposite to the first support plate, and a plurality of positioning rods with equal lengths, one end of which is fixed to the first support plate, while the other end thereof is fixed to the second support plate, the plurality of positioning rods are in parallel with and are perpendicular to the first and second support plates.

In another embodiment, the swing reflection device further comprises a swing position-limit mechanism, to define the range of the swing angle of the swing reflection plate, which comprises a swing member, one end of which is coupled to the driving motor, and a pair of stop parts are disposed on the second support plate, the other end of the swing member is defined to swing between the pair of the stop parts.

Preferably, a rotating shaft is formed on one end of the swing reflection plate, and is rotatably supported on the first support plate through a bearing; the other end of the swing reflection plate is connected to the swing member, to synchronously rotate with the swing member.

In yet another embodiment, the path-folding reflection plate device comprises: a reflection plate; an angle adjusting mechanism configured to adjust an angle of the reflection plate; and a height adjusting mechanism configured to adjust a height of the reflection plate.

Specifically, the height adjusting mechanism comprises: a first double-screw bolt fixed on the main frame of the millimeter-wave inspection apparatus; a second double-screw bolt having a rotation direction opposite to the rotation direction of the first double-screw bolt; a threaded sleeve, which has a lower portion threadedly connected to the first double-screw bolt and an upper portion threadedly connected to the second double-screw bolt, wherein the height of the reflection plate is adjusted by rotating the threaded sleeve; and a locking nut which is capable of locking the height of the height adjusting mechanism.

In one embodiment, the angle adjusting mechanism comprises: a rotating shaft, by which the reflection plate is roatably connected to the top of the second double-screw bolt.

In another embodiment, the path-folding reflection device further includes a position-limit mechanism, to prevent the reflection plate from rotating as the threaded sleeve rotates.

Specifically, the position-limit mechanism comprises: a first position-limit plate, which has an upper end connected to the reflection plate and a lower end with a slot; and a second position-limit plate, which has a lower portion fixed onto the main frame of the millimeter-wave inspection apparatus and an upper portion inserted into the slot at the lower end of the first position-limit plate.

In one embodiment, the convex lens device is a biconvex lens.

In another embodiment, the radiometer receiving device comprises: a linear array of radiometers; first and second positioning plates, which fix the radiometers therebetween by a first fastener; and a support frame configured to condition the angle of the radiometers.

In another embodiment, the millimeter-wave inspection apparatus further comprises a radiometer temperature calibration device, which comprises: a normal temperature calibration mechanism, having a calibration temperature equal to the current environment temperature, to calibrate the initial value of the radiometer; and a high temperature calibration mechanism, having a calibration temperature higher than the current environment temperature, to cooperate with the normal temperature calibration mechanism for calibrating the gain of the radiometer.

Specifically, the normal temperature calibration mechanism comprises a rotatable normal temperature calibration hollow cylinder assembly and a second driving motor mounted onto a bracket, to drive the normal temperature calibration hollow cylinder assembly to continually rotate around the radiometer.

Preferably, the high temperature calibration mechanism comprises a high temperature calibration semi-circular plate assembly and a third driving motor mounted on the bracket to drive the high temperature calibration semi-circular plate assembly to continually swing around the radiometer.

In another embodiment, the normal temperature calibration hollow cylinder assembly and the high temperature calibration semi-circular plate assembly rotate about the same axis, one end of the normal temperature calibration mechanism is attached to the rotating shaft, which in turn is connected to the output shaft of the second driving motor, the shaft end of the rotating shaft is formed with a shafting hole in which a key is formed, and the output shaft of the second driving motor is inserted into the shafting hole of the rotating shaft, thereby achieving a direct connection therebetween.

In one embodiment, the millimeter-wave inspection apparatus further comprises a control device, to control operations of the millimeter-wave inspection apparatus.

In another embodiment, the millimeter-wave inspection apparatus includes a main frame, and the optics devices and the radiometer receiving device are mounted onto the main frame.

In yet another embodiment, the millimeter-wave inspection apparatus further includes a camera which acquires an optical image of the object to be inspected.

Compared with the prior art, since the millimeter-wave is used to perform security inspection in the present invention, the present invention can produce the following technical effect: it would not be harmful to the human health by employing the passive millimeter-wave human body security inspection technology; and the contraband items to be concealed within the human clothing can be efficiently and effectively detected. Moreover, the design of path-folding means is employed, so that the millimeter-wave inspection apparatus becomes more compact.

BRIEF DESCRIPTION OF THE DRAWING

Those and/or other aspect and advantages can be apparent and readily understood from the following description of the preferred embodiment, in combination with the accompanying drawings, wherein:

FIG. 1C is a schematic structure perspective view of the millimeter-wave inspection apparatus as shown in FIGS. 1A and 1B when performing security inspection of human body, in accordance with one embodiment of the present invention;

DETAILED DESCRIPTION OF THE EMBODIMENTS OF THE INVENTION

Figure 1A:
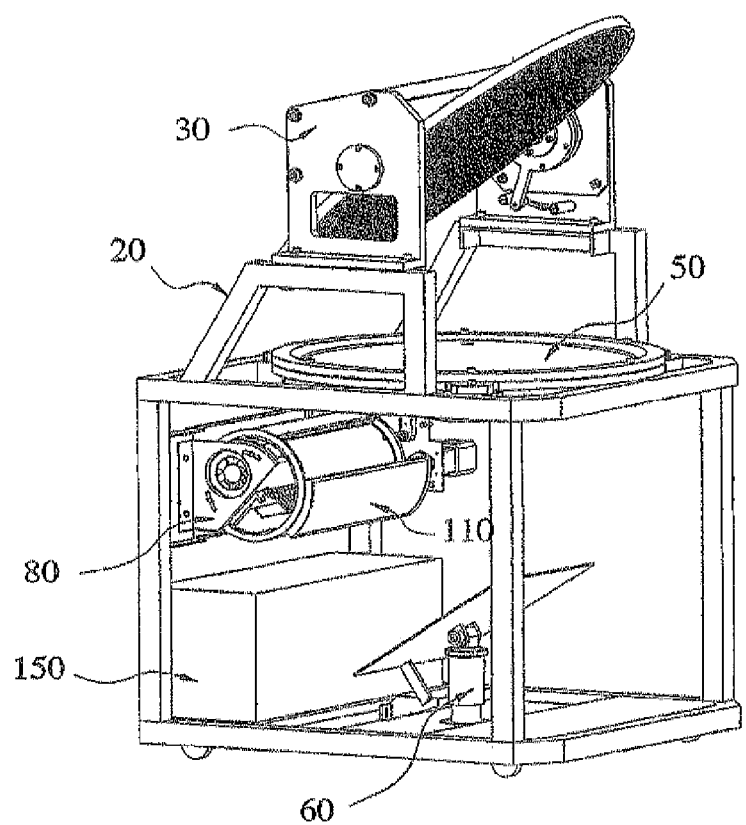
FIG. 1A and FIG. 1B are respectively schematic structure perspective views of a millimeter-wave inspection apparatus in accordance with one embodiment of the present invention.

Specific embodiments of the present invention will be described hereinafter in detail with reference to the specific examples. It is apparent for those skilled in the art to understand configurations, advantages and functionality of the present invention from the disclosure of the following embodiment.

The present invention can also be implemented by or embodied in other different embodiments. Various details of the description can be modified or altered based on different concepts and applications without departing from the spirits of the present invention.

Moreover, the attached drawings are simplified views to schematically convey the basic concept of the present invention. Therefore, the drawing only illustrates the related assembly to the present invention, while failing to delimit the number, shapes and sizes of the assembly as implemented. When implementing the present invention, the shapes, number and the scale can be altered as required, and these may become more complex.

The present invention will now be described more fully hereinafter with reference to the accompanying drawings, in which various embodiments of the invention are shown.

Figure 1B:
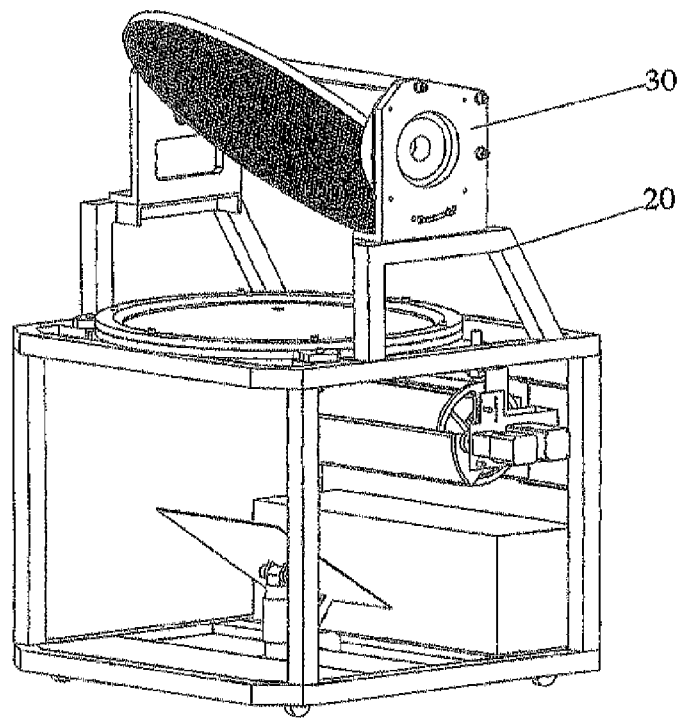
Figure 10:
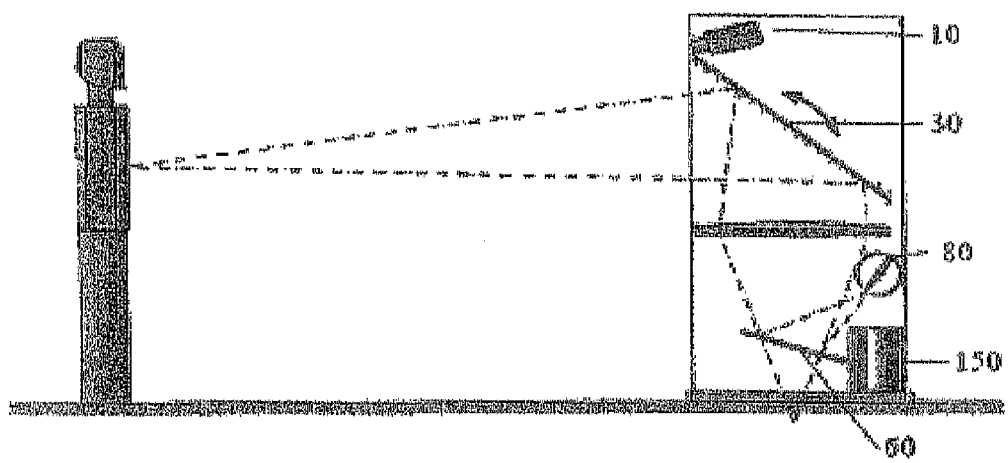

FIGS. 1A and 1B show a millimeter-wave inspection apparatus in accordance with one embodiment of the present invention. Specifically, the millimeter-wave inspection apparatus includes: optics devices 30, 50, 60, configured to receive millimeter-wave energy radiated from an object to be inspected and focus the received millimeter-wave energy; a radiometer receiving device 80 configured to receive the focused millimeter-wave energy and transform the millimeter-wave energy into electrical signal; and an imaging device (not shown) configured to generate a temperature image of the object to be inspected in accordance with the electrical signal. Furthermore, the millimeter-wave inspection apparatus further includes a radiometer temperature calibration device 110, which will be described in detail hereinafter.

It will be appreciated that the millimeter-wave inspection apparatus further includes a control device 150 to control operations of the millimeter-wave inspection apparatus. In particular, the control device 150 sends out control instructions for controlling various components of the millimeter-wave inspection apparatus. The imaging device will transform the electrical signal obtained by the radiometer receiving device 80 into the image information for detection and identification. It is apparent that the imaging device can be embodied in various forms such as computers, microprocessors and display devices.

In addition, the millimeter-wave inspection apparatus further includes a main frame 20 which is used to protect and support various components of the millimeter-wave inspection apparatus. For example, the optics devices 30, 50, 60 and the radiometer receiving device 80 can be mounted onto the main frame 20. The imaging device can be incorporated into the main frame 20, so as to form an integral device. The imaging device can also be electrically connected to the other components so as to achieve remote imaging. It will be appreciated that the imaging device can integrally be formed on the main frame 20, to directly observe the obtained temperature image. Furthermore, the imaging device can also be disposed in other devices of the millimeter-wave inspection apparatus or separated from the millimeter-wave inspection apparatus, as required.

In one embodiment, as shown in FIG. 1C, the millimeter-wave inspection apparatus further includes a camera 10 which acquires an optical image of the object to be inspected. The optical image of the object acquired by the camera 10, as reference information of the human security inspection, can be associated with the temperate image thereof obtained by the millimeter-wave inspection apparatus.

Specifically, the optics device 30, 50, 60 further includes: a swing reflection device 30 configured to receive and reflect the millimeter-wave energy from the object to be inspected; a convex lens device 50 configured to focus the millimeter-wave energy from the swing reflection device 30; and a path-folding reflection plate device 60 configured to fold the propagating path of the focused millimeter-wave energy.

In an embodiment, the convex lens device 50 is a biconvex lens.

Hereinafter, the swing reflection device 30 and the path-folding reflection device 60 of the millimeter-wave inspection apparatus in accordance with the present invention will be described with reference to FIGS. 2 and 3.

Figure 2:
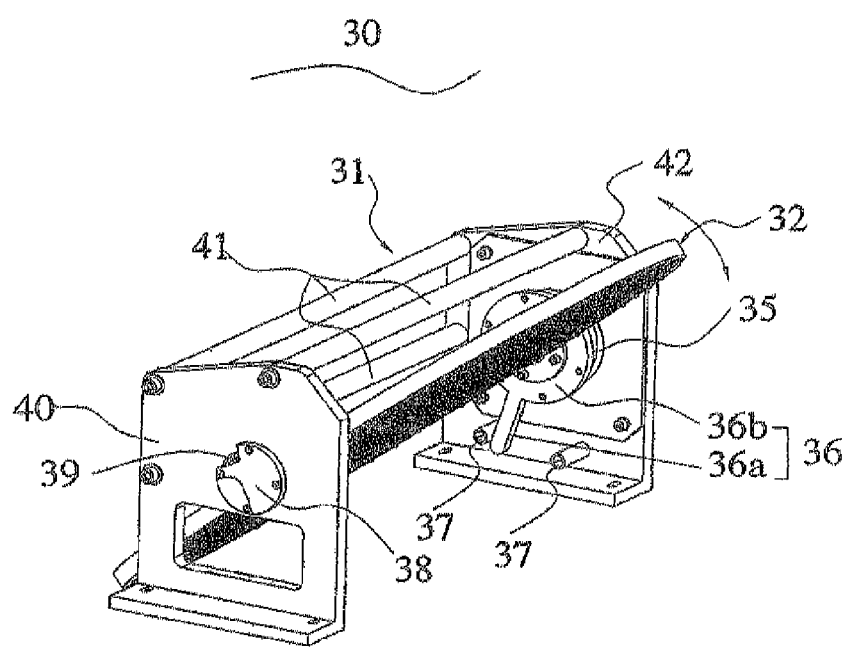
FIG. 2 is a schematic structure perspective view of a swing reflection device of the millimeter-wave inspection apparatus in accordance with one embodiment of the present invention.

As shown in FIG. 2, the swing reflection device 30 shown in the present invention is applied in the millimeter-wave inspection apparatus. However, it is noted that the swing reflection device 30 is also applicable into other apparatus or other applications.

FIG. 2 is a schematic structure prospective view of the swing reflection device 30 in accordance with an exemplary embodiment of the present invention. As shown in FIG. 2, in the embodiment, the swing reflection device 30 mainly includes a support frame 31, a swing reflection plate 32 which is rotatably supported onto the support frame 31; and a driving motor 35, which is connected to the swing reflection plate 32, so as to sway the swing reflection plate 32 back and forth.

The support frame 31 includes a first support plate 40 and a second support plate 42 which are disposed to be in parallel and opposite to each other. Both of the first support plate 40 and the second support plate 42 are fixed onto the main frame 20 of the millimeter-wave inspection apparatus by the threaded connection member such as screws.

In one preferable embodiment, a plurality of positioning rods 41 with equal lengths are provided to ensure to be parallel between the first support plate 40 and the second support plate 42. As shown in FIG. 2, one end of each positioning rod 41 is fixed to the first support plate 40, while the other end thereof is fixed to the second support plate 42.

In FIG. 2, three positioning rods 41 having equal lengths, are provided in the present preferable embodiment. The three positioning rods 41 are in parallel with and are perpendicular to the first and second support plates 40 and 42. But it should be noted that the number of the positioning rods 41 is not limited herein, for example two, three, four or more of the positioning rods 41 can be provided in other embodiments. A bearing hole (not shown) in which a bearing 39 is mounted, is provided on the first support plate 40. The swing reflection plate 32 has a rotating shaft (not shown) at its one end, which is supported by the bearing 39, thereby being rotatably supported in the first support plate 40.

In one preferred embodiment, an end cover 38 is disposed outside of the first support plate 40, in order to prevent the foreign substances such as dust entering into the bearing 39. The end cove 38 is fixed onto the first support plate 40 by screws, so as to cover the bearing hole in which the bearing 39 is mounted.

In one preferred embodiment, the swing reflection device further comprises a swing position-limit mechanism 36, 37, to define the range of the swing angle of the swing reflection plate 32. In the preferred embodiment shown in FIG. 2, the swing position-limit mechanism includes a swing member 36 and a pair of stop parts 37.

As shown in FIG. 2, a driving motor 35 is directly fixed into the interior of the second support plate 42 by the threaded connection members such as screws. Alternatively, the driving motor 35 can be embedded and fixed in the second support plate 42. It is beneficial to reduce the overall volume of the swinging reflection device 30.

In one preferred embodiment, one end of the swing member 36 is directly coupled to the driving motor 35.

Referring to FIG. 2, the pair of stop parts 37 are disposed on the second support plate 42, and the other end of the swing member 36 is confined to swing between the pair of the stop parts 37.

More preferably, the pair of stop parts 37 can be a pair of convex stop posts.

More preferably, elastic sleeves are provided on the pair of stop parts 37 and/or the swing member 36, in order to alleviate or eliminate impact and noise.

In one preferred embodiment, as shown in FIG. 2, the swing member 36 has a circular disc 36b at one end of the swing member 36 and a swing rod 36a at the other end of the swing member 36.

As shown in FIG. 2, a rotatable disc is formed on a rotor of the driving motor 35 in the present preferred embodiment. The circular disc 36b of the swing member 36 is directly and rigidly connected to the rotatable disc of the driving motor 35, thereby achieving the synchronous rotation along with the swing member.

As shown in FIG. 2, the swing reflection plate 32 has a connecting circular disc at the other end. The connecting circular disc of the swing reflection plate 32 is directly and rigidly connected to the circular disc 36b of the swing member 36 by screws, thereby achieving direct and rigid connection with the driving motor 35.

In the above preferred embodiment, as the swing reflection plate 32 is directly and rigidly connected to the driving motor 35 without any other transmission mechanisms, the structure thereof is simple. In addition, the driving motor 35 is capable of driving the swing reflection plate 32 to be swayed back and forth in high-speed.

In another preferred embodiment, the driving motor 35 is a torsion motor. However, the present invention is not limited to this. Other types of motors are possible, such as a stepper motor.

Figure 3:
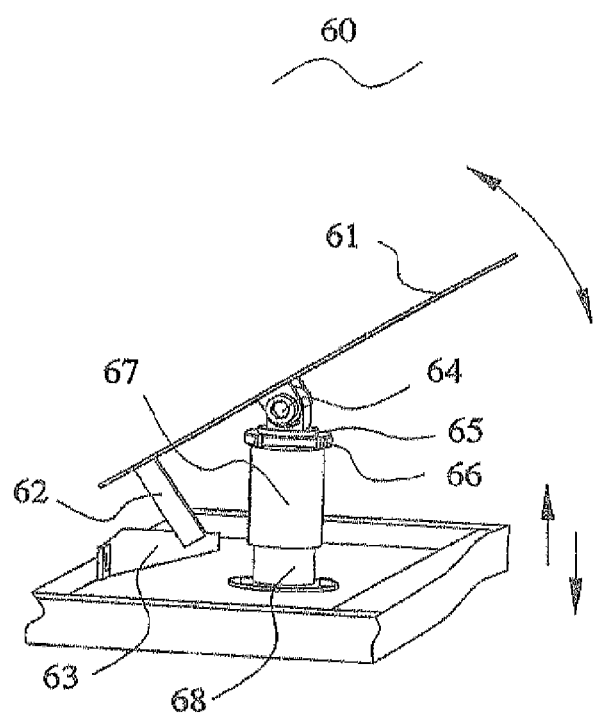
FIG. 3 is a schematic structure perspective view of a path-folding reflection plate device of the millimeter-wave inspection apparatus in accordance with one embodiment of the present invention.

Furthermore, FIG. 3 is a schematic structure perspective view showing the path-folding reflection plate device 60 of the millimeter-wave inspection apparatus in accordance with one embodiment of the present invention.

Specifically, the path-folding reflection plate device 60 includes: a reflection plate 61; an angle adjusting mechanism 64 configured to adjust an angle of the reflection plate 61; and a height adjusting mechanism 65, 67, 68 configured to adjust the height of the reflection plate 61.

Furthermore, the height adjusting mechanism 65, 67, 68 includes: a first double-screw bolt 68 fixed on the main frame 20 of the millimeter-wave inspection apparatus; and a second double-screw bolt 65 having a rotation direction opposite to the rotation direction of the first double-screw bolt 68. The height adjusting mechanism further includes a threaded sleeve 67, which has a lower portion threadedly connected to the first double-screw bolt 68 and an upper portion threadedly connected to the second double-screw bolt 65, wherein the height of the reflection plate 61 is adjusted by rotating the threaded sleeve 67. In addition, the height adjusting mechanism further includes a locking nut 66 which is capable of locking the height of the height adjusting mechanism.

In addition, the angle adjusting mechanism 64 includes a rotating shaft 64, by which the reflection plate 61 is roatably connected to the top of the second double-screw bolt 65. Specifically, the rotation shaft 64 is provided with threads. When it is released, the reflection plate 61 can be adjusted within a certain range of angle.

In one preferred embodiment, the path-folding reflection device 60 further includes a position-limit mechanism 62, 63, in order to prevent the reflection plate 61 from rotating as the threaded sleeve 67 rotates. Specifically, the position-limit mechanism 62, 63 includes a first position-limit plate 62, which has an upper end connected to the reflection plate 61 and a lower end with a slot; and a second position-limit plate 63, which has a lower portion fixed onto the main frame 20 of the millimeter-wave inspection apparatus and an upper portion inserted into the slot at the lower end of the first position-limit plate 62. Thus, the second position-limit plate 63 is embedded in the slot of the first position-limit plate 62, so as to prevent the reflection plate 61 from rotating as the threaded sleeve 67 rotates.

It will be appreciated that when the threaded sleeve 67 rotates, the first double-screw bolt 68 and the second double-screw bolt 65 move in opposite directions at the same time, thereby doubling speed of elevation or dropping.

Figure 4:
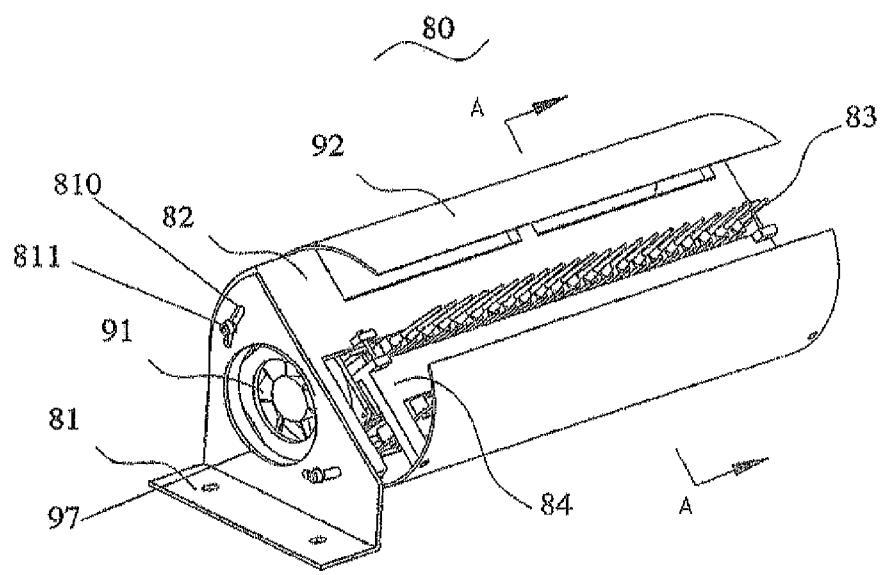
FIG. 4 is a schematic structure perspective view of a radiometer receiving device of the millimeter-wave inspection apparatus in accordance with one embodiment of the present invention.

FIG. 4 shows the radiometer receiving device 80 of the millimeter-wave inspection apparatus in accordance with one embodiment of the present invention. The radiometer receiving device 80 includes: a linear array of radiometers 83; a first and a second positioning plates 82, 84, which fix the radiometers therebetween by a first fastener (not shown, for example screws); and a support frame 81 configured to condition the angle of the radiometers 83.

In particular, the support frame 81 is provided with a sliding hole 810, and the radiometer receiving device 80 further comprises a second fastener 811. The second fastener 811 passes through the sliding hole 810 and connects the support frame 81 to a curved plate of the first positioning plate 82, so that the second fastener 811 can slide within the sliding hole 810 so as to adjust the angle of the first positioning plate 82 and thus to adjust the orientation of the radiometer 83 with respect to the support frame 81.

Furthermore, a fan 91 is disposed within the inner side of the curved plate of the first positioning plate 82, and vent holes 97 corresponding to the fan 91 are provided on the curved plate.

Figure 5:
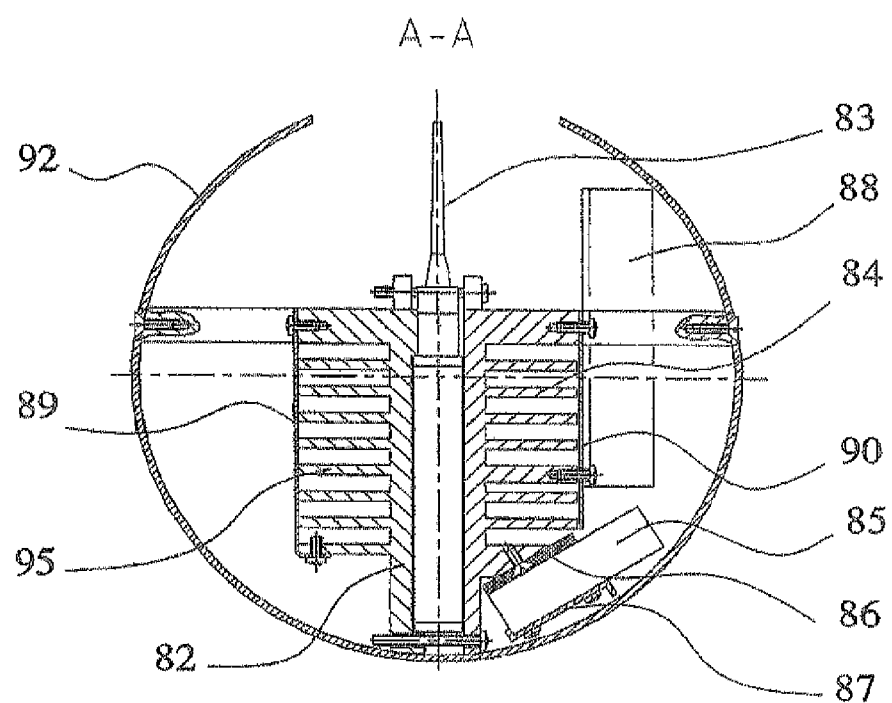
FIG. 5 is a sectional view taken along a line A-A of FIG. 4.

In addition, FIG. 5 is a sectional view along the line A-A of the FIG. 4.

The surfaces of the first and second positioning plates 82 and 84 are respectively disposed with a plurality of heat dissipation fins 95. The radiometer receiving device 80 further comprises air passage clapboards 89, 90 configured to enclose the heat dissipation fins 95 to form air passages. The radiometer receiving device 80 further comprises a shielding cylinder 92, which encloses the first and second positioning plates 82 and 84, as well as the radiometers 83, while leaving a gap in the receiving direction of the radiometer 83.

It is understood that the radiometer receiving device 80 further includes high frequency amplifiers 85 and a high frequency amplifier bracket 86 configured to fix the high frequency amplifiers 85 and a bracket press plate 87. The high frequency amplifier bracket 86 contains grids, and each of the high frequency amplifiers 85 is mounted in each of the grids.

In addition, the radiometer receiving device 80 further comprises a data sampling circuit board 88, which is mounted onto the second positioning plate 84.

It should be understood that the radiometers 83 are arranged at a certain angle depending on the radiation path design. The first and second positioning plates 82, 84 with heat dissipation fins 95 and the air passage clapboards 89, 90 define the heat dissipation air passage, and the heat generated by the radiometer 83 is discharged by the fan 91, to prevent the radiometers 83 from being affected by the environment temperature.

Figure 6:
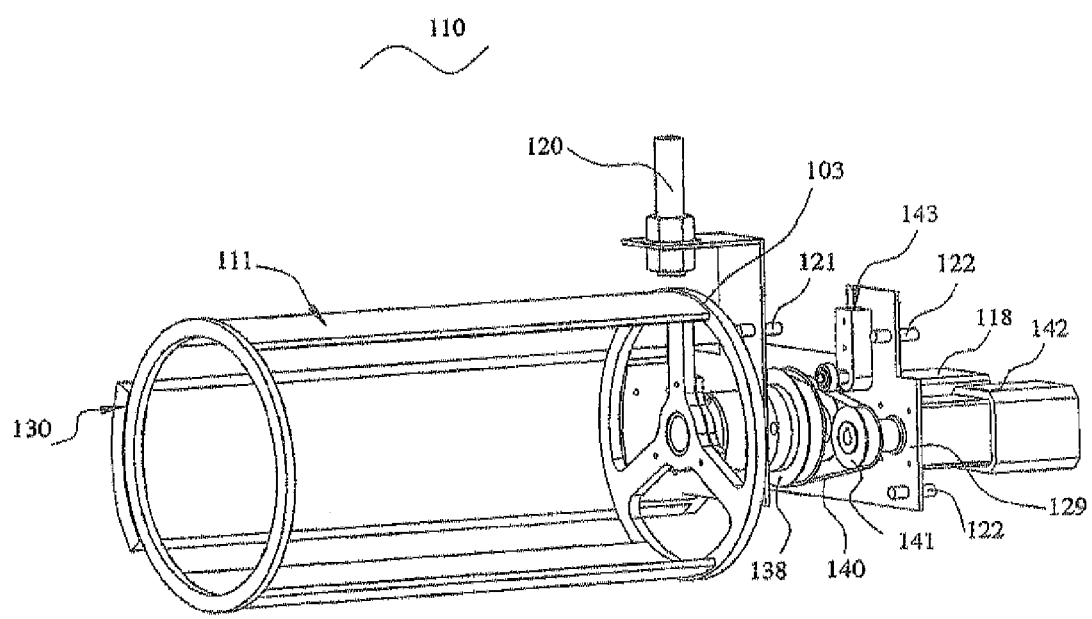
FIG. 6 is a schematic structure perspective view of a high and normal temperatures calibration device of the millimeter-wave inspection apparatus in accordance with one embodiment of the present invention.
Figure 7:
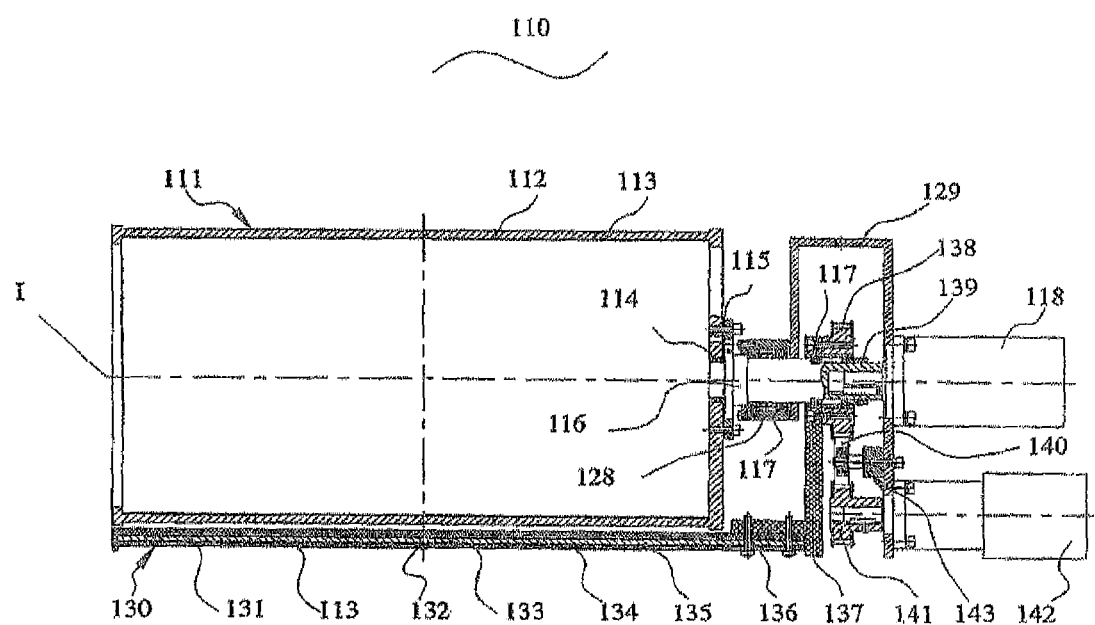
FIG. 7 is a top local sectional view of the high and normal temperatures calibration device of FIG. 6.

FIG. 6 is a schematic structure perspective view showing a high and normal temperatures calibration device of the millimeter-wave inspection apparatus in accordance with one embodiment of the present invention. FIG. 7 is a top local sectional view of the high and normal temperatures calibration device of FIG. 6.

As shown in FIGS. 6 and 7, the radiometer temperature calibration device 110 as shown in the preferred embodiment includes a normal temperature calibration mechanism and a high temperature calibration mechanism. Therefore, herein this radiometer temperature calibration device is referred as the high and low temperatures calibration device. Specifically, the normal temperature calibration mechanism has a calibration temperature equal to the current environment temperature, to calibrate the initial value of the radiometer 83. The high temperature calibration mechanism has a calibration temperature higher than the current environment temperature, to cooperate with the normal temperature calibration mechanism for calibrating the gain of the radiometer 83.

As shown in FIGS. 6 and 7, in one exemplary preferred embodiment, the normal temperature calibration mechanism mainly includes a rotatable normal temperature calibration hollow cylinder assembly 111 and a second driving motor 118. As shown in FIG. 7, the second driving motor 118 is mounted onto a bracket 129, to drive the normal temperature calibration hollow cylinder assembly 111 to continually rotate around the radiometer 83.

As shown, the high temperature calibration mechanism mainly includes a high temperature calibration semi-circular plate assembly 130 and a third driving motor 142.

As shown in FIG. 7, the third driving motor 142 is mounted on the bracket 129 to drive the high temperature calibration semi-circular plate assembly 130 to continually swing around the radiometer 83.

As shown in FIGS. 6 and 7, the high temperature calibration semi-circular plate assembly 130 is disposed outside of the normal temperature calibration hollow cylinder assembly 111, and is separated by a predetermined air gap from the normal temperature calibration hollow cylinder assembly 111, so as to prevent mutual thermal conduction therebetween. Alternatively, the normal temperature calibration mechanism and the high temperature calibration mechanism can also be thermally insulated from each other by thermal insulating materials.

In FIG. 7 as shown in another embodiment, the normal temperature calibration hollow cylinder assembly 111 and the high temperature calibration semi-circular plate assembly 130 rotate about the same axis I.

As shown in FIG. 6, the bracket 129 in the preferred embodiment has a front wall and a rear wall opposed to the front wall. The front wall and the rear wall are connected to each other at one end, to form a U-shaped bracket.

As shown in FIG. 7, the front wall of the bracket 129 is formed with a bearing seat 128. A rotating shaft 116 is rotatably supported in the through hole of the bearing seat 128 by the bearing 117, and the bearing 117 is stopped by a gasket 139.

In one shown preferred embodiment, one end of the normal temperature calibration mechanism 111 is attached to the rotating shaft 116 which is provided with a flange disc. The rotating shaft 116 is connected to the output shaft of the second driving motor 118. Preferably, the shaft end of the rotating shaft 116 is formed with a shafting hole in which a key is provided, and the output shaft of the second driving motor 118 is inserted into the shafting hole of the rotating shaft 116, thereby achieving a direct connection therebetween.

As shown in FIG. 6, the normal temperature calibration mechanism, in one preferred embodiment, further comprises a temperature sensor 120 to detect the temperature of the normal temperature calibration hollow cylinder assembly 111. Preferably, the temperature sensor 120 is fixed on the top of the bracket 129. More preferably, the temperature sensor 120 is an infrared temperature sensor. Alternatively, other types of the temperature sensors can also be employed in the present invention.

In FIG. 6, the normal temperature calibration mechanism further comprises a position sensor 121 to detect the initial position of the normal temperature calibration hollow cylinder assembly 111. Preferably, the position sensor 121 is an approach switch and mounted on the bracket 129. At the same time, a protrusion corresponding to the position sensor 121 is provided on the normal temperature calibration hollow cylinder assembly 111. When the normal temperature calibration hollow cylinder assembly 111 is at the initial position, the position sensor 121 is directly opposite to the protrusion, so as to detect the initial position of the normal temperature calibration hollow cylinder assembly 111.

As shown in FIG. 7, the normal temperature calibration hollow cylinder assembly 111 mainly includes a hollow cylinder 112 and a wave absorbing material 113 disposed inside of the hollow cylinder 112.

As shown in FIG. 7, in one preferred embodiment, the normal temperature calibration mechanism further includes heat insulation devices 114, 115. The heat insulation devices 114, 115 are disposed between the rotating shaft 116 and the one end 103 of the normal temperature calibration hollow cylinder assembly 111, so as to prevent the heat generated by the second driving motor 118 from being conducted to the normal temperature calibration hollow cylinder assembly 111 via the rotating shaft 116.

As shown in FIGS. 6 and 7, one end of the high temperature calibration semi-circular plate assembly 130 is fixed on the first synchronization toothed belt pulley 138 by a sector-shaped bracket 137. The first synchronization toothed belt pulley 138 is rotatably supported on the rotating shaft 116 by a bearing and is connected to the second synchronization toothed belt pulley 141 on the output shaft of the third driving motor 142 by the synchronization toothed belt 140.

As shown in FIG. 7, in one preferable embodiment, the high temperature calibration semi-circular plate assembly 130 includes in turn from the inside to the outside: an insulation sleeve 131, a wave-absorbing material 113, a heat conduction plate 133, a resistance heating film 134, a temperature-retaining material 135 and a heat-insulated plate 136.

As shown in FIG. 7, the high temperature calibration mechanism of one preferred embodiment further includes a temperature sensor 132. The temperature sensor 132 is disposed inside of the high temperature calibration semi-circular plate assembly 130, and contacts with the resistance heating film 134 to detect the temperature of the high temperature calibration semi-circular plate assembly 130.

As shown in FIG. 7, the high temperature calibration mechanism, in one preferred embodiment, further comprises two position-limit detectors 122, to restrict the swing range of the high temperature calibration semi-circular plate assembly 130, so that the high temperature calibration semi-circular plate assembly 130 can swing within the range defined by the pair of the position-limit detectors 122. Preferably, the position-limit detector 122 is a position-limit approach switch.

As shown in FIG. 6, in one preferred embodiment, the high temperature calibration mechanism further includes a tension wheel 143 to adjust the tensile force of the synchronization toothed belt 140. As shown in FIG. 6, the tension wheel 143 is fixed on the bracket 129, and is pressed onto the synchronization toothed belt 140, so that the synchronization toothed belt 140 can be kept in a tension state.

Although the present invention is described in combination with the accompanying drawings, the embodiment disclosed in the accompanying drawings is intended to explain the preferred embodiment as an example, rather than is limitative on the present invention.

Although some embodiments of the general inventive concept are illustrated and explained, it would be appreciated by those skilled in the art that modifications and variations may be made in these embodiments without departing from the principles and spirit of the overall inventive concept of the disclosure, the scope of which is defined in the claims and their equivalents.

What the claims is:

1. A millimeter-wave inspection apparatus, wherein the millimeter-wave inspection apparatus comprises:
   optics devices, configured to receive millimeter-wave energy radiated from an object to be inspected and focus the received millimeter-wave energy;
   a radiometer receiving device configured to receive the focused millimeter-wave energy and transform the millimeter-wave energy into electrical signal;
   an imaging device configured to generate a temperature image of the object to be inspected in accordance with the electrical signal; and
   a radiometer temperature calibration device, which comprises:
      a normal temperature calibration mechanism, having a calibration temperature equal to the current environment temperature, to calibrate the initial value of the radiometer; and
      a high temperature calibration mechanism, having a calibration temperature higher than the current environment temperature, to cooperate with the normal temperature calibration mechanism for calibrating the gain of the radiometer,
      wherein the normal temperature calibration mechanism comprises a rotatable normal temperature calibration hollow cylinder assembly and a second driving motor to drive the normal temperature calibration hollow cylinder assembly to continually rotate around the radiometer.

2. The millimeter-wave inspection apparatus of claim 1, wherein the optics devices, further includes:
   a swing reflection device configured to receive and reflect the millimeter-wave energy from the object to be inspected;

a convex lens device configured to focus the millimeter-wave energy from the swing reflection device; and a path-folding reflection plate device configured to fold the propagating path of the focused millimeter-wave energy.

3. The millimeter-wave inspection apparatus of claim 2, wherein the swing reflection device comprises:
a support frame,
a swing reflection plate which is rotatably supported onto the support frame; and
a first driving motor, which is connected to the swing reflection plate, so as to sway the swing reflection plate back and forth.

4. The millimeter-wave inspection apparatus of claim 3, wherein the support frame comprises:
a first support plate,
a second support plate which is disposed to be in parallel with and opposite to the first support plate, and
a plurality of positioning rods with equal lengths, one end of which is fixed to the first support plate, while the other end thereof is fixed to the second support plate, the plurality of positioning rods are in parallel with and are perpendicular to the first and second support plates.

5. The millimeter-wave inspection apparatus of claim 4, wherein a rotating shaft is formed on one end of the swing reflection plate, and is rotatably supported on the first support plate through a bearing; the other end of the swing reflection plate is connected to the swing member, to synchronously rotate with the swing member.

6. The millimeter-wave inspection apparatus of claim 4, wherein the swing reflection device further comprises:
a swing position-limit mechanism, to define the range of the swing angle of the swing reflection plate, which comprises a swing member, one end of which is coupled to the driving motor, and a pair of stop parts which are disposed on the second support plate, the other end of the swing member is confined to swing between the pair of the stop parts.

7. The millimeter-wave inspection apparatus of claim 2, wherein the path-folding reflection plate device comprises:
a reflection plate;
an angle adjusting mechanism configured to adjust an angle of the reflection plate; and
a height adjusting mechanism configured to adjust the height of the reflection plate.

8. The millimeter-wave inspection apparatus of claim 7, wherein the height adjusting mechanism comprises:
a first double-screw bolt fixed on the main frame of the millimeter-wave inspection apparatus;
a second double-screw bolt having a rotation direction opposite to the rotation direction of the first double-screw bolt;
a threaded sleeve, which has a lower portion threadedly connected to the first double-screw bolt and an upper portion threadedly connected to the second double-screw bolt, wherein the height of the reflection plate is adjusted by rotating the threaded sleeve; and
a locking nut which is capable of locking the height of the height adjusting mechanism.

9. The millimeter-wave inspection apparatus of claim 8, wherein the angle adjusting mechanism comprises:

a rotating shaft, by which the reflection plate is rotatably connected to the top of the second double-screw bolt.

10. The millimeter-wave inspection apparatus of claim 8, wherein the path-folding reflection device further includes a position-limit mechanism, to prevent the reflection plate from rotating as the threaded sleeve rotates.

11. The millimeter-wave inspection apparatus of claim 10, wherein the position-limit mechanism comprises:
a first position-limit plate, which has an upper end connected to the reflection plate and a lower end with a slot; and
a second position-limit plate, which has a lower portion fixed onto the main frame of the millimeter-wave inspection apparatus and an upper portion inserted into the slot at the lower end of the first position-limit plate.

12. The millimeter-wave inspection apparatus of claim 2, wherein the convex lens device is a biconvex lens.

13. The millimeter-wave inspection apparatus of claim 1, wherein the radiometer receiving device comprises:
a linear array of radiometers;
first and second positioning plates, which fix the radiometers therebetween by a first fastener; and
a support frame configured to condition the angle of the radiometers.

14. The millimeter-wave inspection apparatus of claim 1, wherein the second driving motor is mounted onto a bracket.

15. The millimeter-wave inspection apparatus of claim 14, wherein the high temperature calibration mechanism comprises a high temperature calibration semi-circular plate assembly and a third driving motor mounted on the bracket to drive the high temperature calibration semi-circular plate assembly to continually swing around the radiometer.

16. The millimeter-wave inspection apparatus of claim 15, wherein
the normal temperature calibration hollow cylinder assembly and the high temperature calibration semi-circular plate assembly rotate about the same axis, one end of the normal temperature calibration mechanism is attached to the rotating shaft, which in turn is connected to the output shaft of the second driving motor, the shaft end of the rotating shaft is formed with a shafting hole in which a key is provided, and the output shaft of the second driving motor is inserted into the shafting hole of the rotating shaft, thereby achieving a direct connection therebetween.

17. The millimeter-wave inspection apparatus of claim 1, wherein the millimeter-wave inspection apparatus further comprises a control device, to control operations of the millimeter-wave inspection apparatus.

18. The millimeter-wave inspection apparatus of claim 1, wherein the millimeter-wave inspection apparatus includes a main frame, and the optics devices and the radiometer receiving device are mounted onto the main frame.

19. The millimeter-wave inspection apparatus of claim 1, wherein the millimeter-wave inspection apparatus further includes a camera which acquires an optical image of the object to be inspected.

* * * * *